United States Patent [19]
Stricker et al.

[11] Patent Number: 5,633,002
[45] Date of Patent: May 27, 1997

[54] IMPLANTABLE, BIODEGRADABLE SYSTEM FOR RELEASING ACTIVE SUBSTANCE

[75] Inventors: Herbert Stricker, Neckargemund; Gunther Entenmann, Ingelheim am Rhein; Otto Kern, Ingelheim am Rhein; Michel Mikhail, Ingelheim am Rhein; Bernd Zierenberg, Bingen, all of Germany

[73] Assignee: Boehringer Ingelheim GmbH, Ingelheim am Rhein, Germany

[21] Appl. No.: 434,828

[22] Filed: May 4, 1995

Related U.S. Application Data

[63] Continuation of Ser. No. 154,843, Nov. 19, 1993, abandoned, which is a continuation of Ser. No. 881,018, May 8, 1992, abandoned, which is a continuation of Ser. No. 700,721, May 15, 1991, abandoned, which is a continuation of Ser. No. 488,193, Mar. 5, 1990, abandoned, which is a continuation of Ser. No. 253,157, Oct. 4, 1988, abandoned.

[51] Int. Cl.⁶ .......................................................... A61F 2/00
[52] U.S. Cl. .............................................. 424/426; 424/422
[58] Field of Search ........................................ 424/426, 422

[56] References Cited

U.S. PATENT DOCUMENTS

| | | | |
|---|---|---|---|
| 3,317,394 | 5/1967 | Fryklof et al. | 167/82 |
| 3,887,699 | 6/1975 | Yolles | 424/426 |
| 4,166,800 | 9/1979 | Fong | 424/494 |
| 4,767,628 | 8/1988 | Hutchinson | 424/426 |
| 4,830,860 | 5/1989 | Ranade | 424/426 |

FOREIGN PATENT DOCUMENTS

| | | | |
|---|---|---|---|
| 0094513 | 11/1983 | European Pat. Off. | A61K 9/26 |
| 0251476 | 1/1988 | European Pat. Off. | A61K 9/22 |
| 2126270 | 10/1972 | France | A61K 27/00 |

*Primary Examiner*—D. Gabrielle Phelan
*Attorney, Agent, or Firm*—Robert P. Raymond; Wendy E. Rieder; Alan R. Stempel

[57] ABSTRACT

The invention relates to an implantable biodegradable system for releasing active substance.

16 Claims, 6 Drawing Sheets

IMPLANTABLE, BIODEGRADABLE SYSTEM FOR RELEASING ACTIVE SUBSTANCE

This is a continuation of application Ser. No. 154,843, filed Nov. 19, 1993, now abandoned, which is a continuation of application Ser. No. 881,018, filed May 8, 1992, now abandoned, which is a continuation of application Ser. No. 700,721, filed May 15, 1991, now abandoned, which is a continuation of application Ser. No. 488,193, filed Mar. 5, 1990, now abandoned, which is a continuation of application Ser. No. 253,157, filed Oct. 4, 1988, now abandoned.

BACKGROUND OF THE INVENTION

1. Field of the Invention

The invention relates to an implantable biodegradable system for releasing active substance.

2. Description of the Prior Art

Numerous implantable or injectable systems for releasing active substance are known from the prior art. Systems of this kind are preferably used when an active substance has to be administered over a fairly long period of time and oral administration is impossible or unreliable or impractical. In addition to use in humans, parenteral preparations for use in animal husbandry or for the treatment of animal diseases are of special interest. The conventional method of administering drugs by adding them to the feed has the serious disadvantage that the quantity of drug taken is not sufficiently accurate.

Implantable systems for releasing active substance should satisfy the following criteria:

The active substance should be released over a long period of time at a constant rate, the implant should be broken down within a reasonable interval so that there is no need to remove the implant by operating after the active substance has been released. It is also advantageous if the release of active substance from the carrier can be made variable so that the rate of release can be matched both to the active substance and also to the particular treatment.

SUMMARY OF THE INVENTION

The object of this invention is to provide an implantable biodegradable system for releasing active substance which releases the active substance over a fairly long period of time at a substantially constant rate and is broken down within a reasonable time.

This objective is achieved by means of an implant of carrier material based on poly-D,L-lactide containing defined amounts of additives. Suitable additives are pharmacologically acceptable solvents or plasticisers, preferably an acetic acid ester, in an amount of up to 10% and/or a biodegradable low molecular polymer, preferably polylactic acid, in an amount of up to 60% and/or suspended water-soluble pore-forming agents such as lactose in an amount of up to 50%. (All percentages referred to throughout this specification are by weight.)

Poly-D,L-lactides are known over a wide range of molecular weights. For the implant according to the invention, the types of poly-D,L-lactide with a mid-range molecular weight are preferred, having an inherent viscosity of between 0.15 and 4.5. (Inherent viscosities referred to in the specification are determined in chloroform at 25° C. at a test concentration of C=100 mg/100 ml.)

In a preferred embodiment, the carrier material of the implant according to the invention consists of poly-D,L-lactide.

In another embodiment, the implant according to the invention consists of a copolymer of poly-D,L-lactide and polyglycolide, although the proportion of glycolide in the polymer should not exceed 50% by weight.

DETAILED DESCRIPTION OF THE INVENTION

Figure 1:
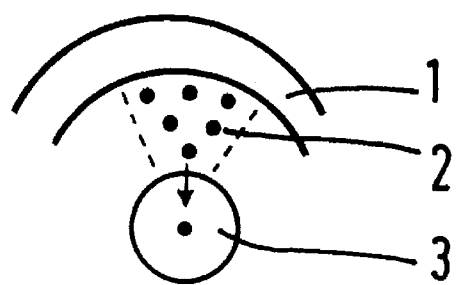
FIG. 1 shows a cross section through one embodiment of the implant according to the invention.

Surprisingly, it has been found that the rate of decomposition of the implant can be controlled by a defined content of acetic acid ester or some other physiologically acceptable solvent or plasticiser or mixture of solvents which will quantitatively remain in the polymer even after lengthy storage. This is of crucial importance, since on the one hand the implant must be broken down rapidly enough but on the other hand excessively rapid decomposition of the implant will lead to uncontrolled release of the active substance. The content of acetic acid ester may be up to 10%, whereby increasing amounts of acetic acid ester will accelerate the breakdown of the poly-D,L-lactide. A release of active substance corresponding to a half-life of between 3 and 60 days followed by breakdown of the implant within about 120 days thereafter would be favorable. In individual cases, naturally, shorter rates of release and breakdown may be advantageous.

It has been found, surprisingly, that the addition of acetic acid ester does influence the rate of decomposition of the implant but has no significant effect on the release of active substance.

Suitable acetic acid esters for the purposes of the invention are the alkyl esters of acetic acid, such as methyl, ethyl, n-propyl, isopropyl, n-butyl, isobutyl, tert.-butyl, n-pentyl, sec.-pentyl, isopentyl and tert.-pentylester. Ethyl acetate is particularly preferred.

In another embodiment, the implant according to the invention may also contain low molecular weight polymers such as, for example, poly(L-lactic acid), poly(D-lactic acid), poly(D,L-lactic acid), poly(glycolic acid), poly(L-lactic acid-co-glycolic acid), poly(D- lactic acid-co-glycolic acid) and poly(D,L-lactic acid-co-glycolic acid). Poly(L-lactic acid) and poly(D,L-lactic acid) are preferred. The molecular weights (determined by titration of the terminal groups) range from 500 to 5000, preferably from 1500 to 2500. (Molecular weights referred to in this specification are number average molecular weights.)

The addition of these substances makes it possible to control the rate of decomposition of the implant when added either on their own or in conjunction with an acetic acid ester.

The rate of release of the active substance can be influenced by various methods:

a) by adding a pore-forming agent, such as lactose or the like.
b) by the state of the active substance (dissolved, suspended, particle size), or
c) by the form which the carrier takes (monolithic, polydispersed, laminated).

In addition to compounds which influence the rate of decomposition of the carrier material, the implant according to the invention also contains substances in the form of pore-forming agents which make it possible to control the release of active substance. Suitable pore-forming agents according to the invention include, for example, water soluble pharmaceutically acceptable monosaccharides and disaccharides. Lactose is preferred, but glucose, fructose, xylose, galactose, sucrose, maltose, saccharose and related compounds such as mannitol, xylitol and sorbitol are also suitable. Other suitable excipients are salts such as lactates, glyconates or succinates of sodium, potassium or magnesium.

Rapid and immediate release of the active substance (as soon as the implant has been put in) from the carrier material is achieved when the rate of release of the pore-forming agent is very much greater than that of the active substance. This is the case, for example, when the pore-forming agent, e.g. lactose, has good solubility and a small particle size.

A less accelerated release of the active substance is achieved when the solubility of the pore-forming agent is very much less than that of the active substance; this occurs, for example, when the pore-forming agent has poor water solubility. This less accelerated release of the active substance ensures that the linear release curve of the active substance is reliably ensured even over long periods of administration.

Using the parameters described, it is possible to produce implants which have an individually adjustable release rate and breakdown rate.

The monolithic implant according to the invention may be implanted or injected in the form of rods or tubular members. The rods are conveniently of such dimensions that they can be implanted by means of an injection needle or a trocar. A rod may be, for example, about 3 cm long and about 2.8 mm in diameter.

The embodiments described hereinafter are preferred:
A) solid rods
B) rolled up films
C) encased rods
D) tubular members
E) encased tubular members All the embodiments of the implant according to the invention may be of laminated construction and may be produced, for example, by the following method.

The active substance is suspended in the dissolved polymer e.g. with ethyl acetate as solvent, and the additives according to the invention are combined therewith. If desired, other pharmaceutical adjuvants may be added to the dissolved polymer in addition to the active substance and the additives. The suspension is then poured out onto a surface and dried to form a film. The drying conditions are chosen so that the desired residual amount of solvent remains in the polymer, generally an amount of between 1 and 7%. The dried films have a layer thickness of between 30 and 1000 micrometers, preferably about 100 micrometers.

Apparatus and methods for producing these films are known to those skilled in the art and require no further comment. It goes without saying that the drying process must be carried out with a certain degree of care (slowly, with minor variations in temperature and vacuum humidity) to ensure that the films stay flat.

Multi-layer films may be obtained by re-applying polymer solution (with or without active substance).

After the film is dry it is cut up into rods of the desired length.

Rods of type B consist of one or more single- or multi-layer polymer films which have been rolled up.

The implant of type B according to the invention is also produced from films containing active substance, although the thickness of the films is substantially less, generally between 30 and 500 micrometers, preferably between 70 and 90 micrometers. After drying, the films are cut and rolled up into rods of the required diameter, up to about 3 mm, which are then cut to the desired length. The rods may be rolled up so that the center contains a space. In the laminate of type B, it is also possible to lay several films one over the other or preferably to pour one over the other and then roll them up to form a rod. By combining several layers of film, active substances can easily be combined and layers with a different concentration of active substance can be produced. The individual layers may have different release rates.

As well as an alternating layer sequence it is also possible to produce a rolled core to begin with and then apply additional layers of film on the outside.

By using layers of film with different release characteristics, it is possible to produce an implant which will release different active substances in a predetermined time sequence. It is not absolutely necessary for all the film layers to contain active substances.

When producing the implant of type B according to the invention, the films should have a relatively high content of residual solvent (about 10%) when they are rolled up. This prevents the films from becoming brittle. Once rolled up, the rod is then subjected once more to a drying process in order to achieve the desired content of residual solvent.

Implants of type C, D and E are advantageously produced by extrusion or injection moulding of granules of active substance and polymer or copolymer, optionally with additives such as polylactic acid, a plasticiser such as triacetin or a pore-forming agent such as lactose.

The release of active substance from the encased forms C and E takes place by various methods depending on the construction used. The active substance in suspended form in the core of the encased rods of form C diffuses through pores in the casing which are caused by dissolving out of lactose, for example. The critical release factors are therefore the degree of charging of the casing and the particle size of the lactose.

By contrast with the encased forms of type C which contain a solid core containing the active substance and are surrounded by a "porous" casing, the implants of type E consist of a hollow cylinder (tube) containing the active substance, the outer surface of which is encased in a sheath which is impermeable to the active substance.

In form E, the active substance suspended in the tubular member can only be released into the space in the body (tube), provided that the casing is free from pores and impervious. In this system, the channels, i.e. diffusion paths, which become longer as time goes on, are compensated by the quantity of active substance in a segment, which is greater the longer the distance from the cylinder axis.

FIG. 1 shows a cross section through embodiment E according to the invention.

The crucial release factors in this case, in addition to the breakdown of the polymer and the degree of charging, are the dimensions such as the lengths and internal diameter of the tubular implant. It goes without saying that, in the case of implants of type E, the casing which is impervious to the active substance also consists of a biodegradable polymer, preferably a poly-D,L-lactide. A major advantage of the implants thus formed is that the active substance is released in a substantially linear manner.

Implants of this type may also be produced on the basis of the films described hereinbefore, the outer film consisting of a layer which is free from active substance and impervious to active substance.

Findings have hitherto shown that the implants (type A and B) produced by the "solvent method" have different breakdown characteristics from the extruded members, i.e. the extruded members are broken down more slowly despite having the same polymer composition (cf. FIG. 1). The difference is due to the fact that it is not possible to achieve a defined, higher content of residual solvent because of the relatively high temperatures during extrusion.

Active substance release systems according to the invention (implants) produced by extrusion or injection moulding may conveniently be produced based on a poly-D,L-lactide having an inherent viscosity of between 0.15 and 1.0. Polymers of low inherent viscosity ($\eta=0.15$) may be processed even at temperatures below 100° C., which is advantageous for the thermal stress on the drugs added thereto.

Implants produced from a low viscosity poly-D,L-lactide not only release the active substance more rapidly but also show faster decomposition of the implant than is the case with higher inherent viscosities (greater than 0.3), which means that an implant may have broken down after only 10 weeks, if desired.

Low viscosity poly-D,L-lactides may be prepared from higher viscosity poly-D,L-lactides by partial hydrolysis.

The release of active substance from the implants according to the invention may be delayed by an additional coating of low molecular poly-D,L-lactide which contains no active substance but which is permeable to the active substance. This prevents the active substance from being released too quickly in the initial phase directly after implanting.

Suitable active substances are those which occur in suspended form in the polymer, especially the water-soluble salt forms of bases such as hydrochlorides or hydrobromides. Clenbuterol hydrochloride is particularly preferred.

Furthermore, in the field of veterinary medicine, the groups of substances and compounds listed below may be used in the implants according to the invention.

Glucocorticoids for inducing labour, e.g. dexamethasone, betamethasone, flumethasone, the esters and derivatives thereof, gestagens for synchronising heat, or for suppressing heat and rut, $\beta_2$-adrenergics for the treatment and prevention of respiratory diseases, for preventing abortion and birth, for promoting growth and influencing the metabolism, such as clenbuterol, ethyl 4-(2-tert.-butylamino-1-hydroxyethyl)-2-cyano-6-fluoro-phenylcarbamate hydrochloride, α-[[[3-(1-benzimidazolyl)-1,1-dimethylpropyl]-amino]-methyl-2-fluoro-4-hydroxy-benzylalcohol methanesulphonate monohydrate, 1-(4-amino-3-cyanophenyl)-2-isopropylaminoethanol, β-blockers for the prevention of Mastitus Metritas Agalactie, for reducing travel stress, α2-adrenergics against enteritic diseases and for the treatment of hypoglycaemic conditions, and for sedative purposes (e.g. clonidine, 2-[2-bromo-6-fluoro-phenylimino]-imidazolidine, benzodiazepines and derivatives thereof such as brotizolam for sedative purposes, antiphlogistics for anti-inflammatory treatment, e.g. meloxicam, somatotropin and other peptide hormones for increasing yield, endorphins for stimulating movement in the rumen, steroid hormones (natural and synthetic) for promoting growth, e.g. oestradiol, progesterone and the esters and synthetic derivatives thereof such as trenbolon, anti-parasitics for controlling endo- and ectoparasites, such as avermectin, cardiac and circulatory substances such as etilefrin or pimobendan.

The implants according to the invention may advantageously used in human medicine for administering hormones, particularly for contraception or as cytostatics.

It is possible to use active substances which have both a systemic and a local effect.

A preferred field of use of the implants according to the invention is local cancer therapy.

In the Examples which follow the invention is explained more fully by means of Examples.

In the Examples the following polymers are used.

Polymer materials used are:

| | | | | |
|---|---|---|---|---|
| D,L-polylactide I [η] = | 1.0 | (100 ml/g = | MW* = | 123,000 |
| D,L-polylactide II [η] = | 2.2 | (100 ml/g = | MW = | 300,000 |
| D,L-polylactide III | | | MW = | 11,500 |
| D,L-polylactic acid (MW = | 2000) | | | |

*Determined by gas phase chromatography (standard: polystyrene)

[η]=intrinsic or limiting viscosity

EXAMPLE 1

(Factors of polymer decomposition: method of processing, tacticity, molecular mass)

25 g of D,L-polylactide I are dissolved in 75 g of ethyl acetate and spread out with a doctor blade on a smooth surface to form a film. After drying for at least 24 hours this is repeated twice or three times until a multi-layer film 250 micrometers thick has been produced. The film is then dried first at 23° C. and then at 40° C. in vacuo until a predetermined residual solvent content is obtained, cut into 3×2.5 cm pieces and shaped into rolls (3 cm long, 2.8 mm diameter).

Figure 2:
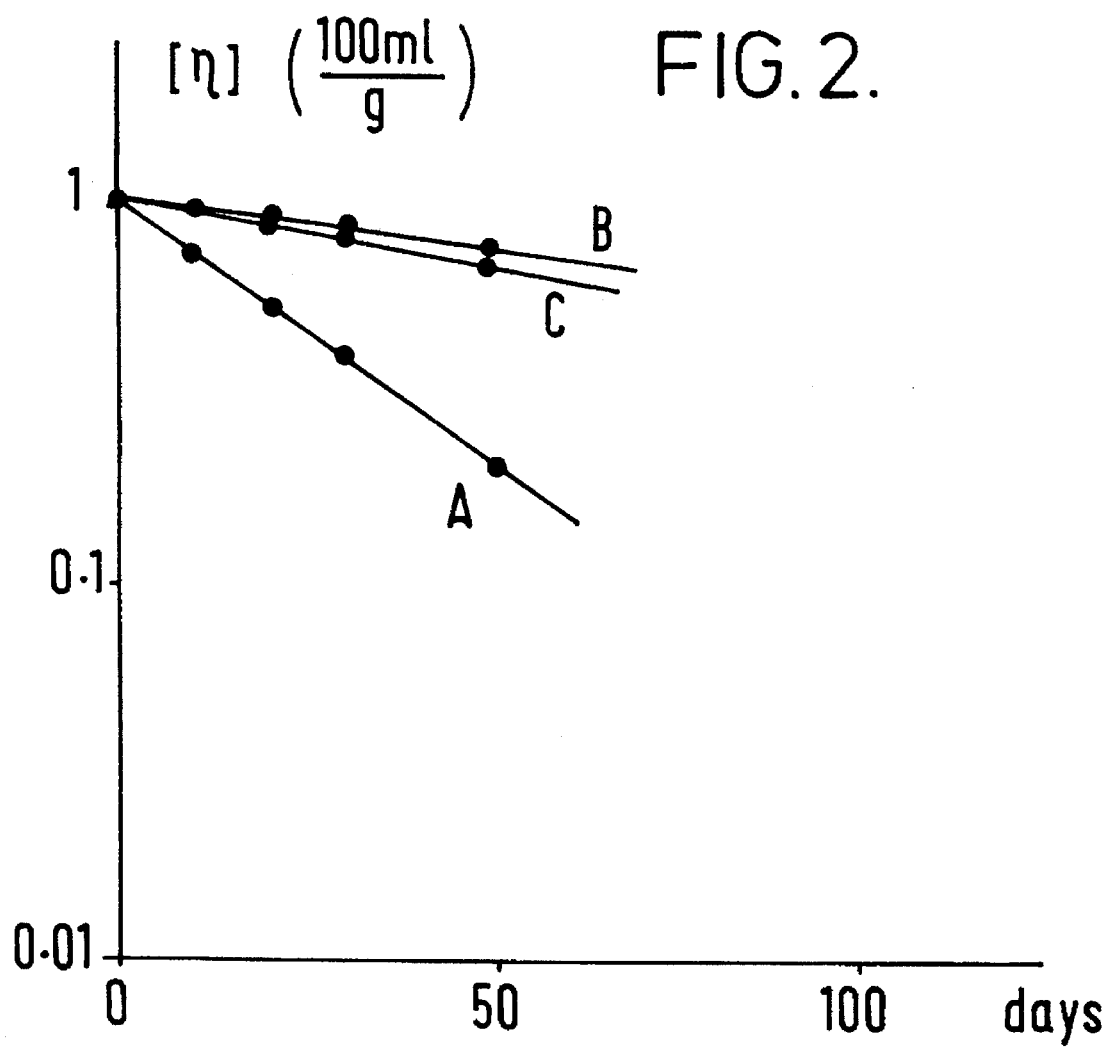
FIGS. 2, 7 and 11 are graphs showing the reduction in mass of various polylactide implants according to the invention, as a function of time, when placed in an isotonic phosphate buffer solution.
Figure 3:
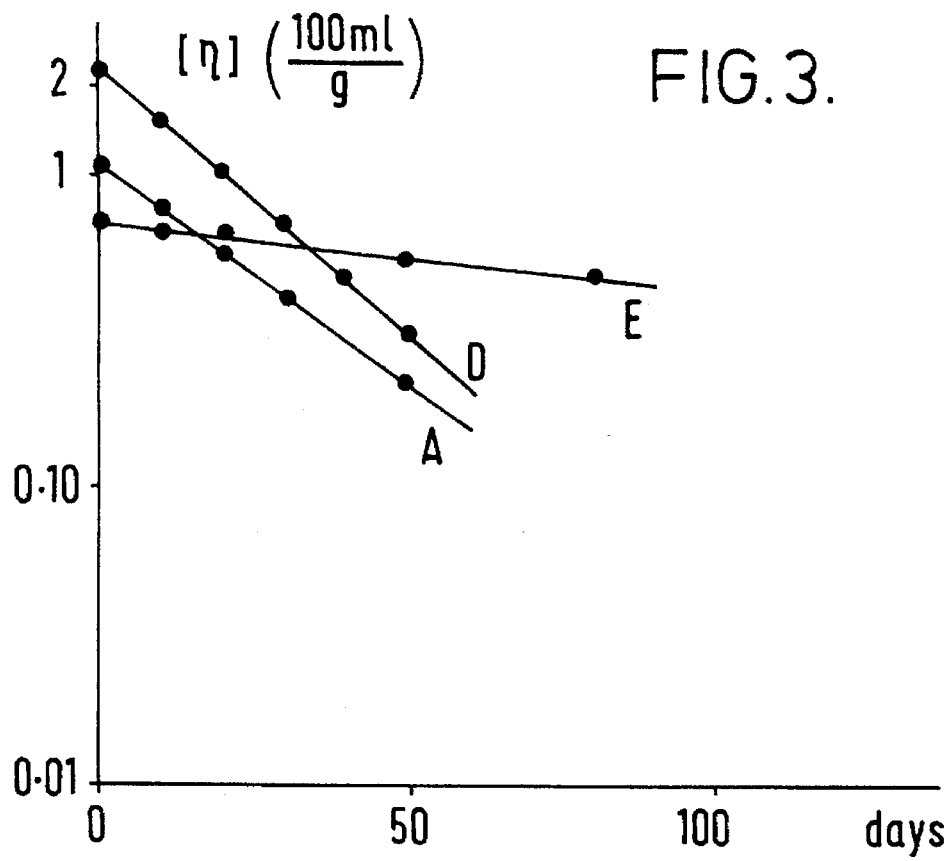
FIG. 3 is a graph showing the reduction in molecular mass of various polylactide implants, as a function of time, when placed in an isotonic phosphate buffer solution.

Implants produced by the solvent method have different characteristics than implants obtained by extrusion, for example, with regard to their decrease in molecular mass in a buffer solution, i.e. they are advantageously broken down more rapidly (FIG. 1). The tacticity of the polymer plays a greater part in the rate of breakdown than the molar mass or intrinsic or limiting viscosity [η] (FIG. 2). The fact that the rate of breakdown in vitro corresponds well to the in vivo values is shown by FIG. 3.

Figure 4:
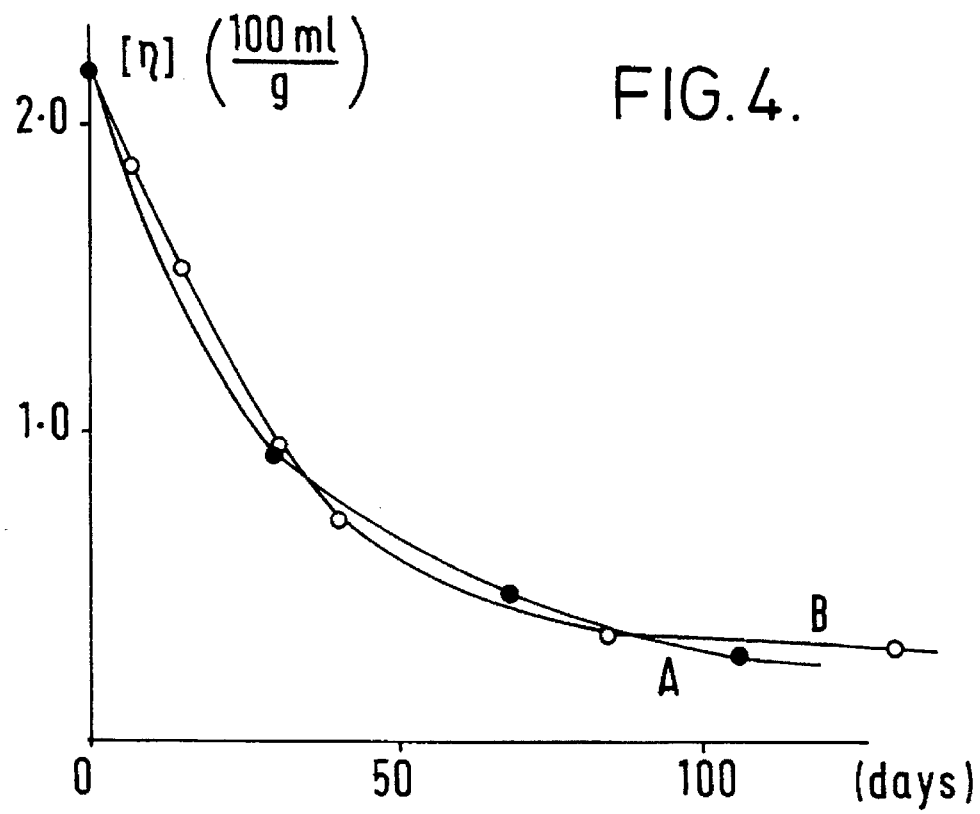
FIG. 4 is a graph showing the reduction in molecular mass of D,L-polylactide implants, as a function of time, when placed in an isotonic phosphate buffer solution and when administered in vivo, sheep, s.c.

A significant reduction in mass occurs after about 70 days both in vivo and in vitro, i.e. after the limiting viscosity has fallen to a value of [η] 0.3 (100 ml/g) (see FIG. 4).

The administration of the implants to sheep, rats and mice did not produce any special reactions over the observation period (up to 140 days), i.e. the implants were well tolerated locally (Table 1).

Instead of using the solvent method, correspondingly constructed shaped articles may also be produced by extrusion (core with casing) of granules of polymer, active substance and additives.

EXAMPLE 2

(Factors of polymer breakdown: residual content of ethyl acetate, addition of polylactic acid)

Multi-layer rolls of film are produced as described in Example 1, except that in batch I 50% of the D,L-polylactide are replaced by D,L-polylactic acid (molecular mass 2000).

Figure 5:
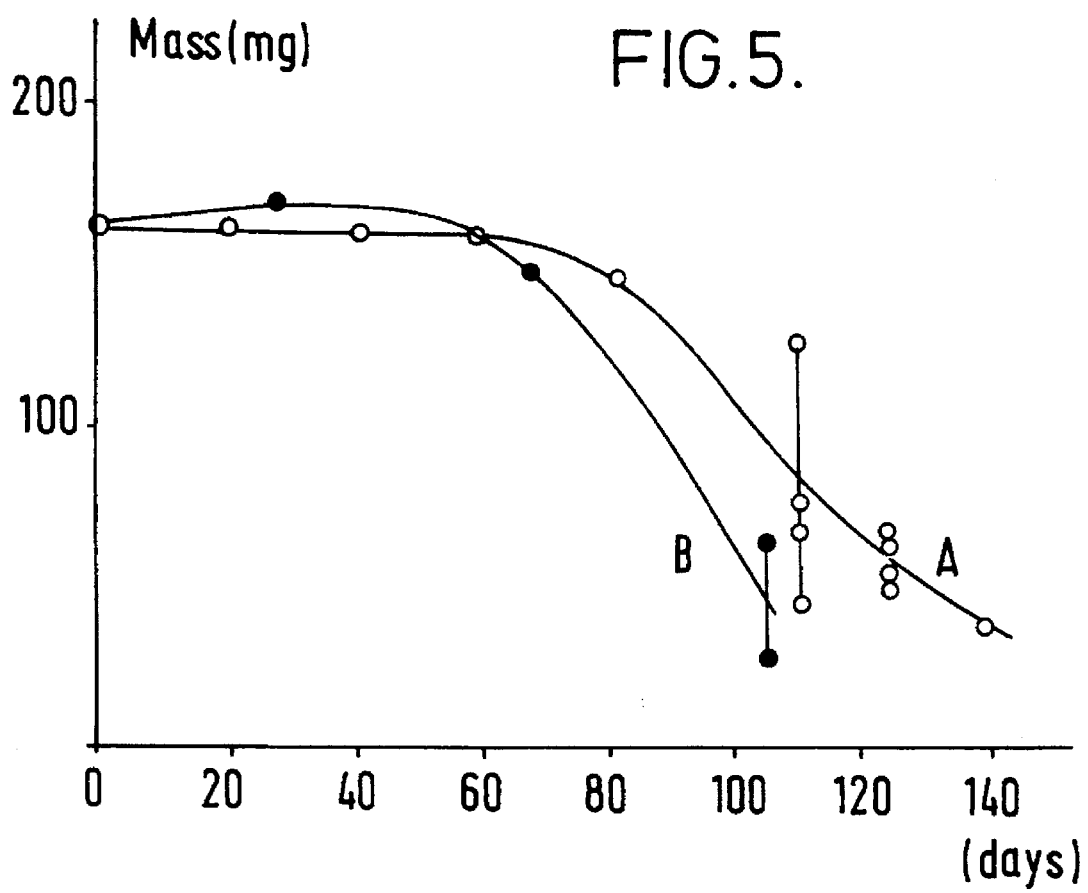
FIG. 5 is a graph showing the reduction in mass of D,L-polylactide implants, as a function of time, when placed in an isotonic phosphate buffer solution and when administered in vivo, sheep, s.c.

FIG. 5 shows that the decrease in molecular mass in an aqueous medium is accelerated by a residual ethyl acetate content of 4 or 7% but not by a content of 1%. The addition of 50% of D,L-polylactic acid has a very marked effect in this respect.

Figure 6:
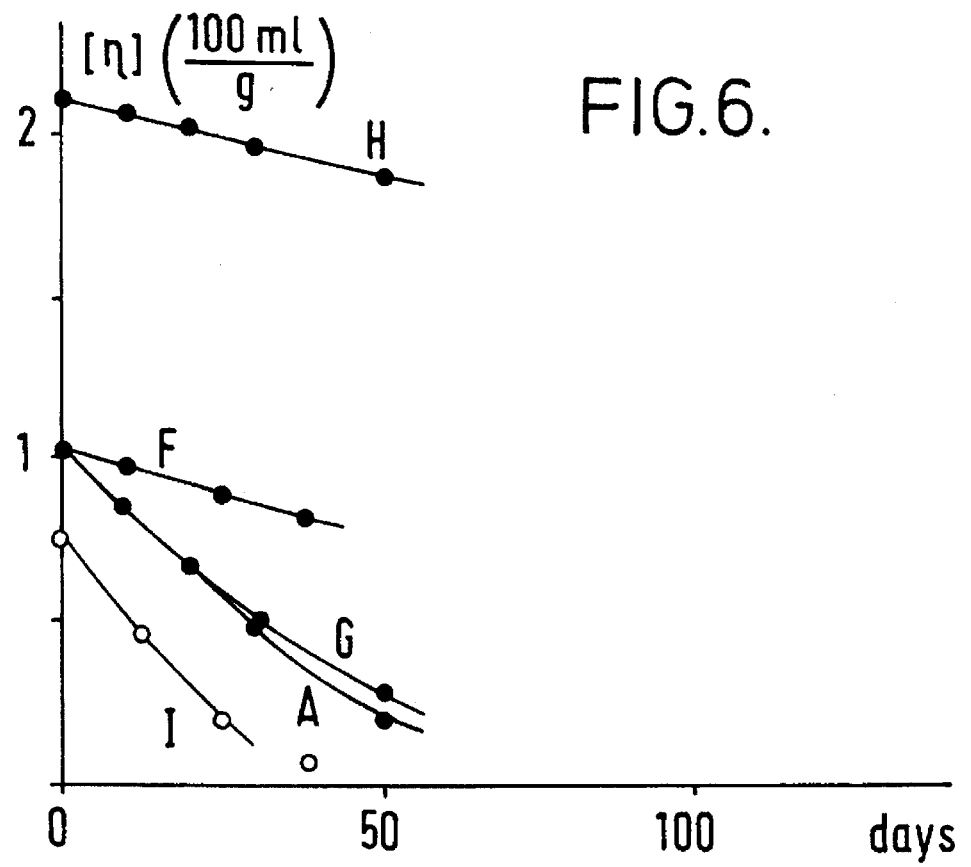
FIG. 6 is a graph showing the reduction in molecular mass of various D,L-polylactide implants, as a function of time, when placed in an isotonic phosphate buffer solution and when administered in vivo in sheep, s.c.

The reduction in mass correlates with the reduction in molecular mass as described in Example 1 (FIG. 6).

EXAMPLE 3

(Factor of release of substance: structure of substrate) 25 g of D,L-polylactide II ($[\eta]$=2.2 (100 ml/g)) are dissolved in 75 g of ethyl acetate, 5.0 g of methotrexate (MTX) (particle size 30 micrometers=x=60 micrometers) are suspended therein and three-layer films are produced with a layer thickness of 0.80 mm analogously to Example 1, the upper and lower layers of polymer remaining free from active substance. After the residual solvent content of 7% has been obtained, the multi-layer film is cut into strips of 1×1×10 mm, unlike Example 1.

Figure 7:
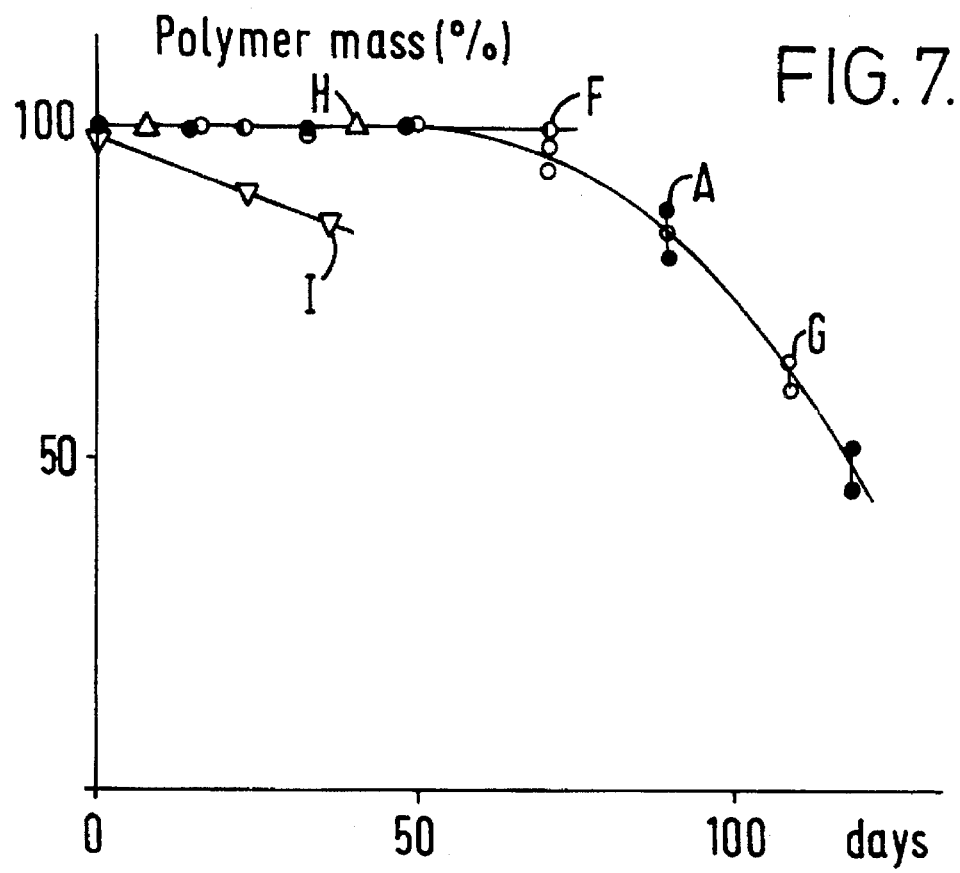

From implants of this kind, MTX is released at a constant rate of 63 micrograms per day in the period from 10 to about 60 days, both in vivo and in vitro, without any significant reduction in the polymer mass (FIG. 7).

EXAMPLE 4

(Factor of release of substance: addition of lactose)

8.8 g of D,L-polylactide II ($[\eta]$=2.2 (100 ml/g)) are dissolved in 45 g of ethyl acetate and 2.7 g of clenbuterol-.HCl (20 micrometers=x=53 micrometers) are suspended therein and a three-layer film is prepared as in Example 1. In batch L, an additional 25% by weight of lactose (1–5 micrometers) are suspended in the polymer solution for the central layer.

Figure 8:
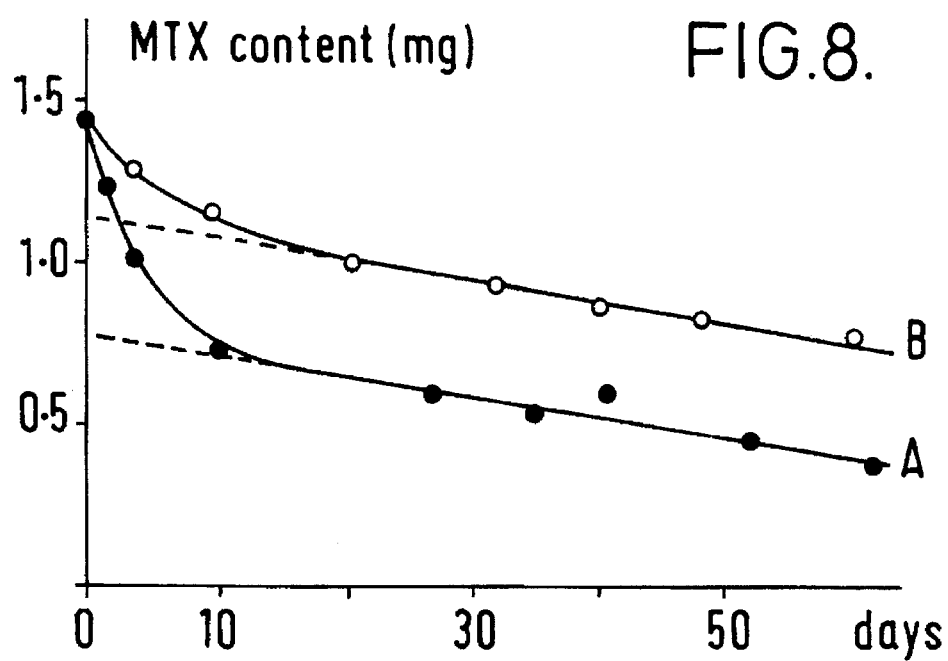
FIG. 8 is a graph showing the release of methotrexate from polylactide implants according to the invention, as a function of time.
Figure 9:
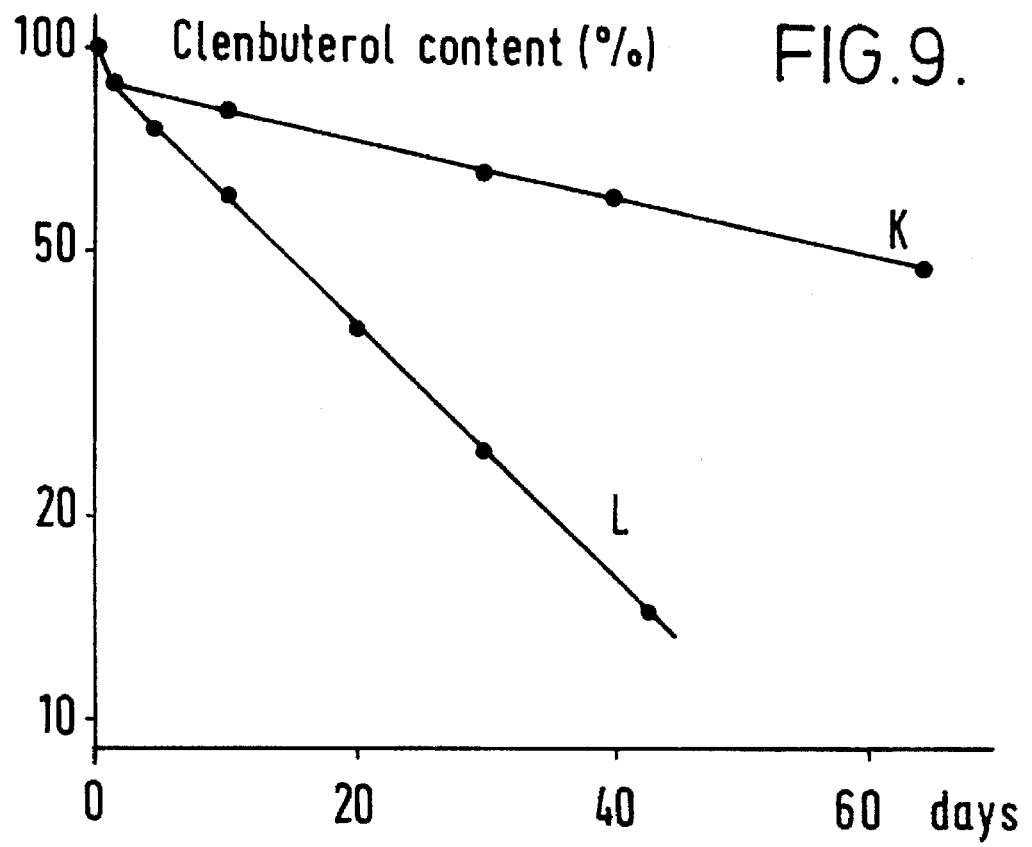
FIGS. 9, 10 and 12 are graphs showing the release of clenbuterol from polylactide implants according to the invention, as a function of time.

FIG. 8 shows that the addition of lactose accelerates the release of clenbuterol in an aqueous medium and thus provides a method of controlling the release.

EXAMPLE 5

(Factor of release of substance: addition of polylactic acid)

The three-layered film roll L of Example 4 is compared with a preparation produced analogously in which 25% of the D,L-polylactide II is replaced by D,L- polylactic acid (molecular mass 2000).

Whereas the release of clenbuterol in an aqueous medium is greatly accelerated by the addition of polylactic acid, the residual ethyl acetate content in the range from 1–4% had no effect on the release characteristics.

Polylactic acid can therefore be used like lactose as an additive which will control the release.

EXAMPLE 6

(Factor of release of substance: structure of substrate) (embodiment E)

D,L-polylactide III with no active substance and a fusion granulate consisting of 3 parts by weight of D,L-polylactide III and 1 part by weight of clenbuterol (hydrochloride, 20–53 micrometers) are processed at 90° C. (mass temperature) to form a double-walled tube (this can be done both by using a suitable extruder or by injection moulding). An implant in the form E—produced according to Example 6—having the following dimensions was used for in vitro tests on the breakdown of polymer and release of active substance: length 10 mm, diameter of central space 2 mm, overall diameter 5 mm; outer casing free from active substance and impervious, wall thickness 0.5 mm; inner tube containing active substance, wall thickness 1.0 mm.

Figure 10:
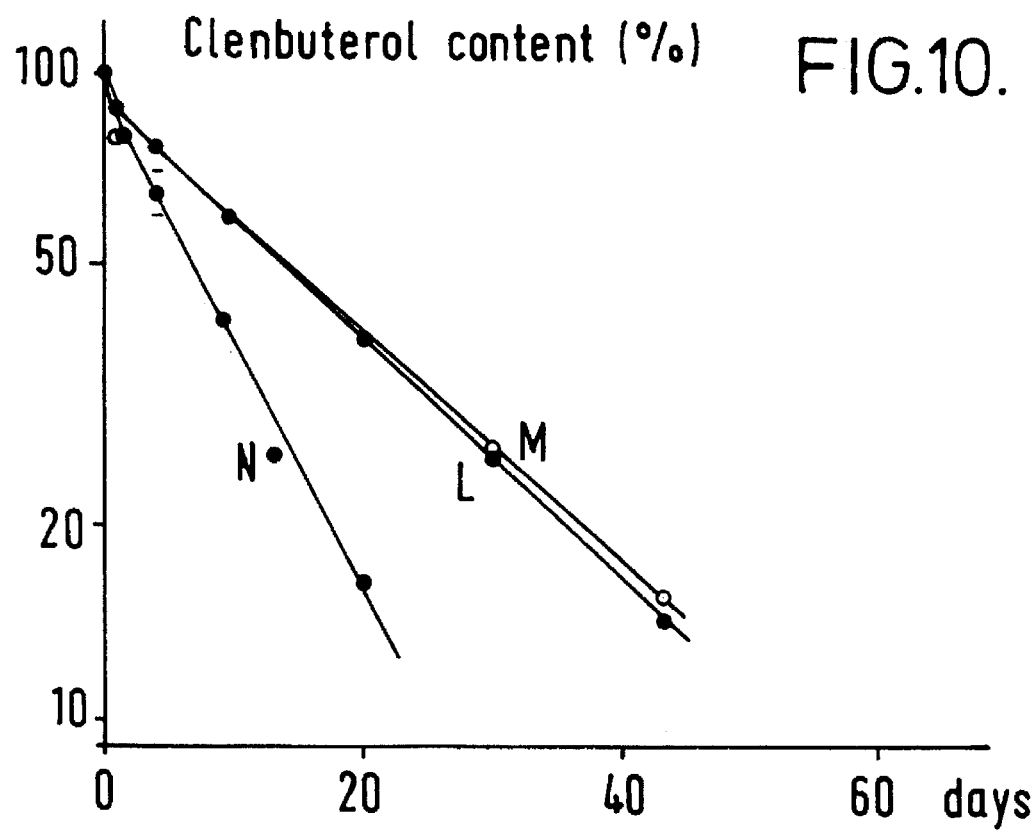
Figure 11:
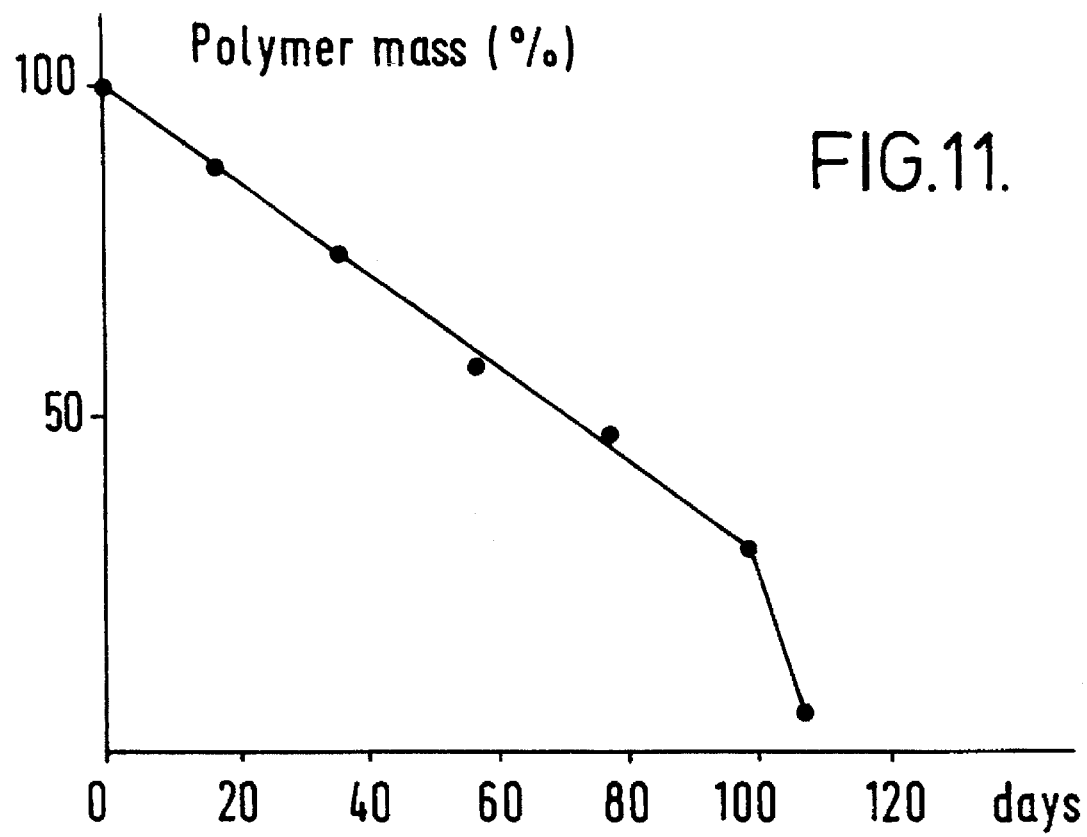
Figure 12:
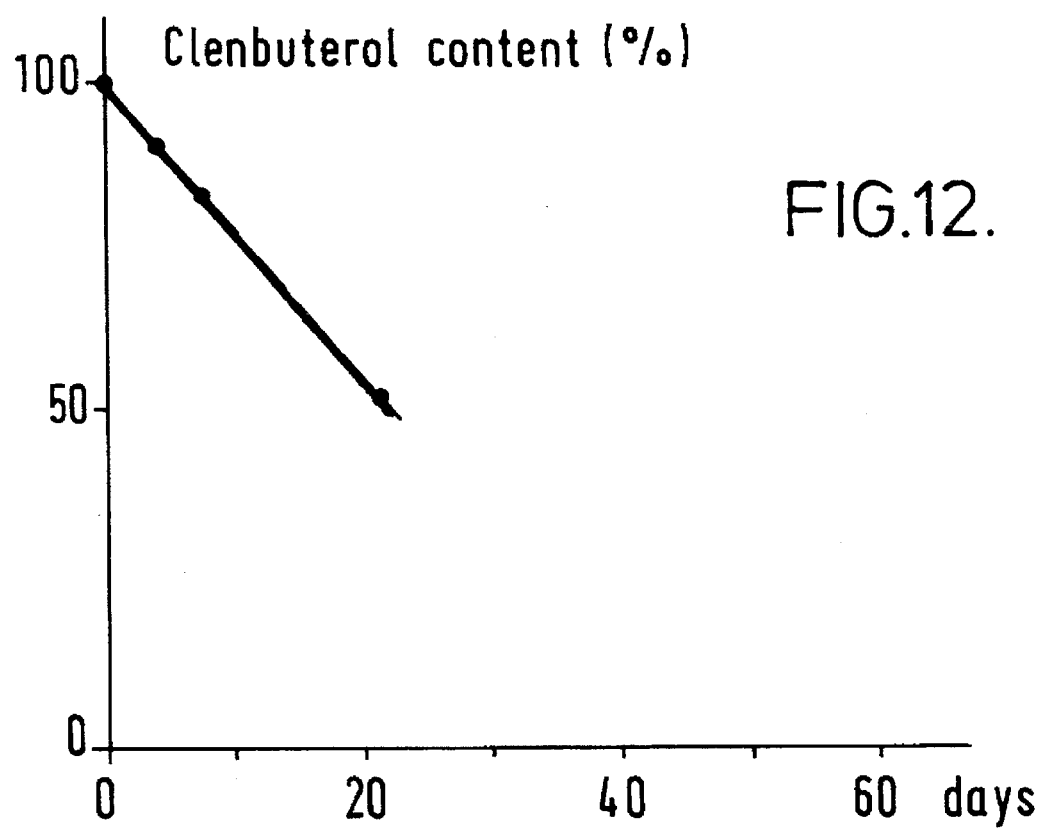

FIG. 10 describes the substantially linear breakdown of the polymer mass in vitro with a half life of about 70 days whilst FIG. 11 shows the substantially linear release of clenbuterol.

TABLE I

| Pathology and histology of the implants | | | |
| --- | --- | --- | --- |
| | | Findings | |
| Species | Administration | up to about 60 days: slight capsule formation, slight inflammation, usual macrophage formation individual cell detritus | from about 100 days: slight scarring, no inflammation and no other findings |
| Sheep | s.c., behind the ear | reaction normal | yes |
| Mouse | s.c. neck | reaction normal | yes |
| | s.c. back | reaction normal | yes |
| Rat | intra-cerebral | reaction normal | yes |
| | intra-tumoral, back | reaction normal | yes |

What is claimed is:

1. An implantable, biodegradable system for releasing an active substance, said system comprising a carrier material based on biodegradable poly-D,L-lactide and an active substance incorporated therein, wherein the carrier material contains from 1 to 10% by weight of a physiologically harmless ester of acetic acid, and wherein said active substance is released by biodegradation of the carrier.

2. The system for releasing an active substance as claimed in claim 1, wherein the carrier material is based upon a copolymer of D,L-lactide and glycolide, in which the glycolide content does not exceed 50% by weight.

3. The system for releasing an active substance as claimed in claim 1 or 2, wherein the acetic acid ester is ethyl acetate.

4. The system for releasing an active substance as claimed in claim 3, wherein the carrier material contains polylactic acid having a molecular weight in the range between 500 to 5000 number average molecular weight, and lactose.

5. The system for releasing an active substance as claimed in claim 4, characterized in that it takes the form of a rod which has a multi-layer structure.

6. The system for releasing an active substance as claimed in claim 5, characterized in that it comprises multiple layers of rolled film.

7. The system for releasing an active substance as claimed in claim 4, characterized in that it comprises a hollow cylinder or tube containing the active substance and an outer casing which is impermeable to the active substance, so that the active substance is released through the cavity in the cylinder.

8. The implantable, biodegradable system for releasing an active substance of claim 1 wherein the carrier material contains a pore forming agent.

9. The implantable, biodegradable system for releasing an active substance of claim 1 wherein the acetic acid esters are alkyl esters.

10. The implantable, biodegradable system for releasing an active substance, in accordance with claim 9, wherein the alkyl esters of acetic acid are selected from the group consisting of methyl, ethyl, n-propyl, isopropyl, n-butyl, isobutyl, tert.-butyl, n-pentyl, sec.-pentyl, isopentyl and tert.-pentyl ester.

11. The system for releasing an active substance as claimed in claim 1, wherein the carrier material contains from 1 to 7% by weight of an acetic acid ester.

12. The system for releasing an active substance as claimed in claim 1, wherein the carrier material contains from 4 to 10% by weight of an acetic acid ester.

13. The system for releasing an active substance as claimed in claim 1, wherein the carrier material contains from 4 to 7% by weight of an acetic acid ester.

14. The system for releasing an active substance as claimed in claim 13, wherein the carrier material contains 4% by weight of an acetic acid ester.

15. The system for releasing an active substance as claimed in claim 13, wherein, the carrier material contains 7% by weight of an acetic acid ester.

16. The system for releasing an active substance as claimed in claim 11, 12, 13, 14 or 15, wherein the acetic acid ester is ethyl acetate.

* * * * *